United States Patent
Schotzko et al.

(10) Patent No.: US 11,642,173 B2
(45) Date of Patent: May 9, 2023

(54) IMAGE-BASED NAVIGATION SYSTEM AND METHOD OF USING SAME

(71) Applicant: Medtronic, Inc., Minneapolis, MN (US)

(72) Inventors: Elizabeth A. Schotzko, Blaine, MN (US); Linnea R. Lentz, Stacy, MN (US); Sarah E. Ahlberg, Maple Grove, MN (US); Syed Omar Ishrak, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 148 days.

(21) Appl. No.: 16/433,507

(22) Filed: Jun. 6, 2019

(65) Prior Publication Data
US 2019/0307518 A1 Oct. 10, 2019

Related U.S. Application Data

(63) Continuation of application No. 16/376,636, filed on Apr. 5, 2019.
(Continued)

(51) Int. Cl.
*A61B 34/20* (2016.01)
*A61B 90/00* (2016.01)
(Continued)

(52) U.S. Cl.
CPC .............. *A61B 34/20* (2016.02); *A61B 8/085* (2013.01); *A61B 8/0841* (2013.01);
(Continued)

(58) Field of Classification Search
CPC ....... A61B 34/20; A61B 8/0841; A61B 34/25; A61B 8/463; A61B 8/085; A61B 8/4254;
(Continued)

(56) References Cited

U.S. PATENT DOCUMENTS 6,216,029 B1 4/2001 Paltieli
6,470,207 B1 10/2002 Simon et al.
(Continued)

FOREIGN PATENT DOCUMENTS

EP 2900131 A2 8/2015

OTHER PUBLICATIONS

Razzaque et al., "Navigating for Image-Guided Ablation: Exploring its Unique Application and Associated Challenges," Medtronic, Boulder, CO, 2017, 11 pages.
(Continued)

*Primary Examiner* — Yi-Shan Yang
*Assistant Examiner* — Nicholas A Robinson
(74) *Attorney, Agent, or Firm* — Mueting Raasch Group

(57) ABSTRACT

Various embodiments of a system for guiding an instrument through a region of a patient are disclosed. The system includes an instrument and a controller that is adapted to receive ultrasound image data from an ultrasound sensor, receive EM tracking data from an EM tracking system, and identify a physiological landmark of the region of the patient based on the ultrasound image data. The controller is further adapted to determine at least one of a position, orientation, or trajectory of the instrument based on the EM tracking data and generate a graphical user interface showing at least one of the position, orientation, or trajectory of the instrument in relation to a plane of the ultrasound image data, and a target zone that is registered with the physiological landmark.

22 Claims, 12 Drawing Sheets

Related U.S. Application Data

(60) Provisional application No. 62/653,988, filed on Apr. 6, 2018.

(51) Int. Cl.
  *A61B 8/08* (2006.01)
  *G16H 30/40* (2018.01)
  *A61B 34/00* (2016.01)
  *A61B 8/00* (2006.01)
  *G16H 40/63* (2018.01)
  *G16H 20/40* (2018.01)
  *A61B 34/10* (2016.01)

(52) U.S. Cl.
  CPC ............ *A61B 8/4254* (2013.01); *A61B 8/463* (2013.01); *A61B 8/5207* (2013.01); *A61B 34/25* (2016.02); *A61B 90/39* (2016.02); *G16H 20/40* (2018.01); *G16H 30/40* (2018.01); *G16H 40/63* (2018.01); *A61B 8/0883* (2013.01); *A61B 8/467* (2013.01); *A61B 2034/107* (2016.02); *A61B 2034/2051* (2016.02); *A61B 2090/365* (2016.02); *A61B 2090/378* (2016.02); *A61B 2090/3925* (2016.02)

(58) Field of Classification Search
  CPC ..... A61B 90/39; A61B 8/5207; A61B 8/0883; A61B 8/467; A61B 2034/107; A61B 2090/378; A61B 2090/365; A61B 2034/2051; A61B 2090/3925; G16H 30/40; G16H 40/63; G16H 20/40
  See application file for complete search history.

(56) References Cited

U.S. PATENT DOCUMENTS

| | | |
|---|---|---|
| 8,046,052 B2 | 10/2011 | Verard et al. |
| 8,340,379 B2 | 12/2012 | Razzaque et al. |
| 8,401,616 B2 | 3/2013 | Verard et al. |
| 8,467,853 B2 | 6/2013 | Hunter et al. |
| 8,842,893 B2 | 9/2014 | Teichman et al. |
| 9,504,531 B2 | 11/2016 | Teichman et al. |
| 2004/0097805 A1* | 5/2004 | Verard ................ A61B 8/4254 600/428 |
| 2010/0268085 A1 | 10/2010 | Kruecker |
| 2011/0081063 A1* | 4/2011 | Leroy ................ A61B 8/0841 382/131 |
| 2011/0125020 A1* | 5/2011 | Kondou ................ A61B 8/5261 600/443 |
| 2012/0215108 A1 | 8/2012 | Park |
| 2013/0197357 A1* | 8/2013 | Green ................ A61B 34/10 600/424 |
| 2016/0174873 A1 | 6/2016 | Greenburg et al. |
| 2016/0324580 A1* | 11/2016 | Esterberg ............... A61B 34/10 |
| 2017/0124700 A1* | 5/2017 | Sarojam ................... A61B 8/46 |
| 2017/0135760 A1 | 5/2017 | Girotto et al. |
| 2017/0316561 A1 | 11/2017 | Helm et al. |
| 2018/0161013 A1* | 6/2018 | Monk ................... G06T 7/248 |
| 2020/0054399 A1* | 2/2020 | Duindam ............... A61B 34/25 |
| 2020/0268347 A1* | 8/2020 | Kolen ................... G06T 7/0012 |

OTHER PUBLICATIONS (PCT/US2019/026022) PCT Notification of Transmittal of the International Search Report and the Written Opinion of the International Searching Authority, dated Aug. 6, 2019, 18 pages.

* cited by examiner

IMAGE-BASED NAVIGATION SYSTEM AND METHOD OF USING SAME

CROSS-REFERENCE TO RELATED APPLICATION

This is a continuation application of U.S. patent application Ser. No. 16/376,636, filed Apr. 5, 2019, which claims the benefit of U.S. Provisional Application No. 62/653,988, filed Apr. 6, 2018, the disclosures of which are incorporated by reference herein in its entirety.

BACKGROUND

Echocardiography and other types of imaging systems can be difficult to use and interpret, especially for implanters (cardiac surgeons) of mechanical circulatory support (e.g. LVAD) devices and various other types of transcatheter or minimally-invasive technologies (e.g., coronary stents, heart valves, ablation devices, cardiac leads). Currently, many surgeons do not use echocardiography during these types of procedures because of inherent shortcomings of this type of imaging system (e.g., difficult to interpret, poor image quality, etc.). Further, clinicians are increasingly utilizing more minimally-invasive techniques for implanting cardiac devices in contrast to open heart surgery and sternotomies. These minimally-invasive techniques require improved imaging systems as the clinician does not have a line-of-sight view of the patient's heart during the implantation procedure.

Image-guided medical and surgical procedures utilize patient images obtained prior to or during a medical procedure to guide a clinician performing the procedure. Recent advances in imaging technology, especially in imaging technologies that produce highly-detailed, two, three, and four-dimensional images, such as computed tomography (CT), magnetic resonance imaging (MRI), isocentric C-arm fluoroscopic imaging, positron emission tomography (PET), and ultrasound imaging (US), have heightened the interest in image-guided medical procedures.

At present, cardiac catheterization procedures are typically performed with the aid of fluoroscopic images. Two-dimensional fluoroscopic images taken intra-procedurally allow a physician to visualize the location of a catheter being advanced through cardiovascular structures. Use of such fluoroscopic imaging throughout a procedure, however, exposes both the patient and the operating room staff to radiation and exposes the patient to contrast agents. As a result, the number of fluoroscopic images taken during a procedure is preferably limited to reduce the radiation exposure to the patient and staff. Additionally, since fluoroscopy does not visualize cardiac tissue very well, it is relied upon mostly for visualizing blood with contrast dye injected into it. Therefore, fluoroscopy is not the imaging modality of choice for procedures that require a detailed understanding of the location and motion of cardiac tissue.

An image-guided surgical navigation system that enables the physician to see the location of an instrument relative to a patient's anatomy, without the need to acquire real-time fluoroscopic images throughout the surgical procedure, is generally disclosed in U.S. Pat. No. 6,470,207, entitled NAVIGATIONAL GUIDANCE VIA COMPUTER-ASSISTED FLUOROSCOPIC IMAGING, issued Oct. 22, 2002. In this system, representations of surgical instruments are overlaid on pre-acquired fluoroscopic images of a patient based on the position of the instruments as determined by a tracking sensor.

Other types of procedures include the use of electrophysiologic mapping catheters to map the heart based on measured electrical potentials. Such mapping catheters are useful in identifying an area of tissue that is either conducting normally or abnormally; however, some mapping catheters may not aid in guiding a medical device to a targeted tissue area for medical treatment.

SUMMARY

In general, the present disclosure provides various embodiments of a system for guiding an instrument through a region of a patient and a method of using the system. The system can include various imaging and tracking systems and a controller that is adapted to utilize data from these imaging and tracking systems and generate a graphical user interface (GUI). Such GUI can provide any suitable information to a clinician that is performing a medical procedure. For example, in one or more embodiments, the controller can generate a GUI that shows at least one of a position, orientation, or and trajectory of an instrument as the clinician guides the instrument into and out of the region of a patient in relation to a plane or 3D image of the region. The controller can also be adapted to provide one or more markers or target zones in the GUI to guide the clinician to the target region of the patient.

In one aspect, the present disclosure provides a system for guiding an instrument through a region of a patient. The system includes an instrument, an ultrasound sensor configured to collect ultrasound image data, and an electromagnetic (EM) tracking system configured to collect EM tracking data representative of positions and orientations of each of the ultrasound sensor and the instrument relative to the region of the patient. The system also includes a controller adapted to receive the ultrasound image data from the ultrasound sensor, receive the EM tracking data from the EM tracking system, identify a physiological landmark of the region of the patient based on the ultrasound image data, and determine at least one of a position, orientation, or trajectory of the instrument based on the EM tracking data. The controller is further adapted to generate a graphical user interface showing at least one of a position, orientation, or trajectory of the instrument in relation to a plane of the ultrasound image data, and a target zone that is registered with the physiological landmark.

In another aspect, the present disclosure provides a method for guiding an instrument through a region of a patient. The method includes receiving ultrasound image data from an ultrasound sensor, receiving EM tracking data from an EM tracking system representative of positions and orientations of each of the ultrasound sensor and the instrument relative to the region of the patient, and identifying a physiological landmark of the patient. The method further includes determining at least one of a position, orientation, or trajectory of the instrument based on the EM tracking data, and generating a graphical user interface showing at least one of the position, orientation, or trajectory of the instrument relative to a plane of the ultrasound image data, and a target zone that is registered with the physiological landmark.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
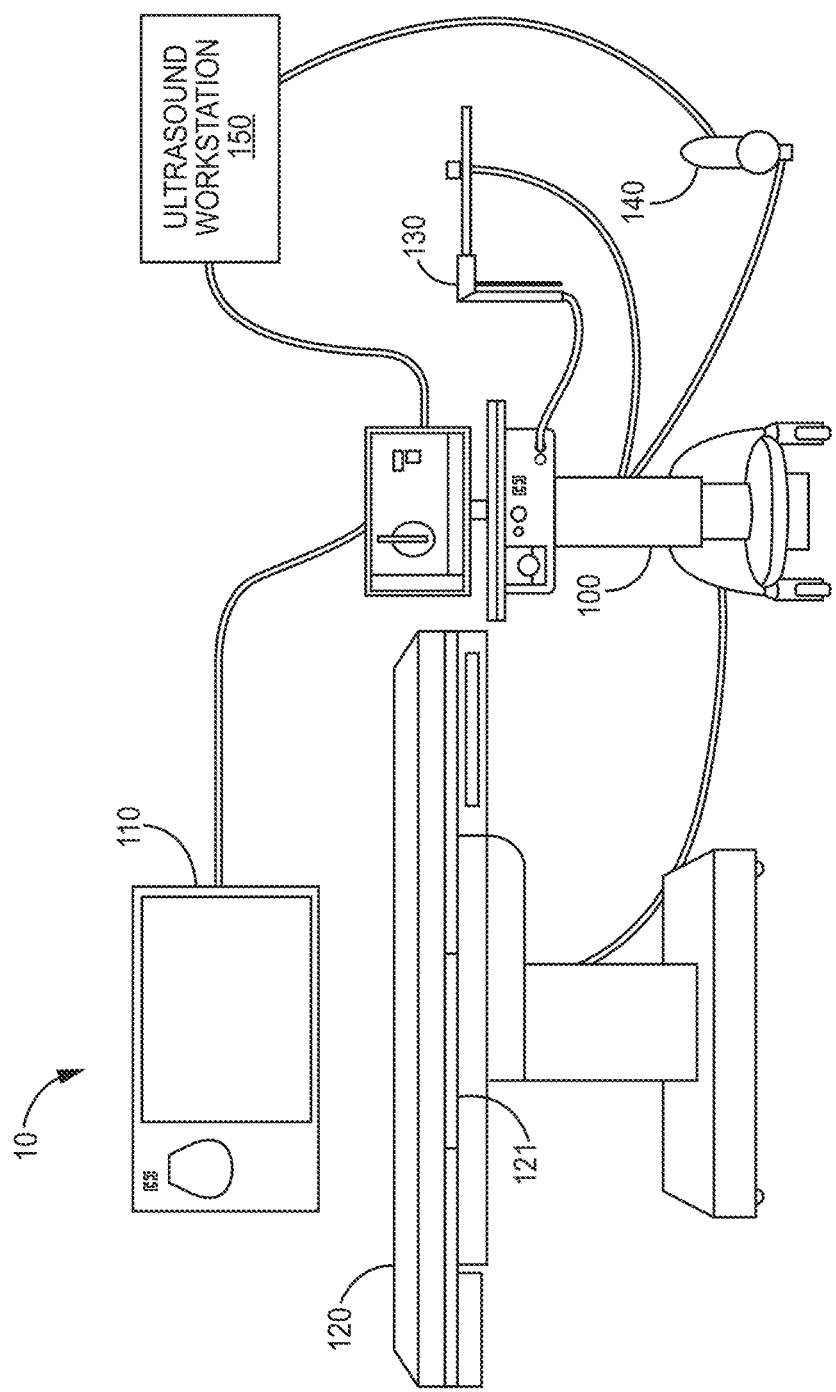
FIG. 1 is a schematic perspective view of one embodiment of a system for guiding an instrument through a region of a patient.

In general, the present disclosure provides various embodiments of a system for guiding an instrument through a region of a patient and a method of using the system. The system can include various imaging and tracking systems and a controller that is adapted to utilize data from these imaging and tracking systems and generate a graphical user interface (GUI). Such GUI can provide any suitable information to a clinician that is performing a medical procedure. For example, in one or more embodiments, the controller can generate a GUI that shows at least one of a position, orientation, and trajectory of an instrument in relation to a plane or 3D image of the region as the clinician guides the instrument into and out of the region of a patient. The controller can also be adapted to provide one or more markers or target zones in the GUI to guide the clinician to a target region of the patient and/or to identify a target region of the patient. The one or more markers or target zones can remain visible in the GUI even if the actual target region of the patient becomes obstructed or unavailable to the imaging system. In one or more embodiments, the controller can overlay or merge one or more reference images of the target region of the patient with one or more live images from the imaging system of the target region of the patient. In one or more embodiments, the controller is adapted to overlay or merge the reference image to the live image such that the reference image is dynamic with the live image. In other words, the reference image is merged with the live image such that the reference image moves in registration with the live image in the GUI. The reference image can remain visible in the GUI even if one or more portions of the live image of the target region becomes obstructed or unavailable to the imaging system.

With regard to navigating an instrument or medical device through a moving body structure, difficulties can arise in attempting to track such an instrument or medical device using known tracking technology as the instrument or medical device passes adjacent or through the moving body structure, and the virtual representation of the instrument or medical device may be offset from the corresponding anatomy when superimposed onto image data. Accordingly, it may be desirable to acquire image data and track the instrument or medical device in a synchronized manner with a pre-acquired image using gating or synchronization techniques such as ECG gating or respiratory gating. Additionally, in situations where the instrument or medical device is highly visible to the imaging technology, the instrument or medical device may obstruct the view of the anatomy of interest (e.g., the target or landing zone for a medical implant); therefore, it can be desirable to identify and track the anatomy that is targeted for therapy delivery during an image-guided procedure.

In one or more embodiments, the present disclosure can provide a system for guiding an instrument through a region of a patient while identifying and tracking a region of anatomy of the patient during a medical procedure (e.g., an ablation procedure, a valve placement procedure, a lead placement procedure, an LVAD placement procedure, etc.). The system can include various imaging and tracking systems and a controller that incorporates machine learning to identify a region of a patient utilizing data from these imaging and tracking systems and that is adapted to generate a GUI that can include one or more markers representing one or more target zones to guide the clinician to the target region of interest of the patient. Once the target region of interest of the patient is identified based on the medical procedure and the use of machine learning, one or more markers (e.g., a marker signifying a point or a plane) can be placed in the GUI to represent the target or landing zone of interest for the medical procedure. In one or more embodiments, a marker indicating the target region can also visually change when an instrument reaches the target zone (e.g., target zone changes color from red to green). This can be beneficial especially when the anatomy of interest is not visible. The one or more anatomical markers in the GUI can remain visible even if the target region of the patient becomes obstructed or unavailable to the ultrasound sensor collecting ultrasound image data. The one or more anatomical markers in the GUI can be utilized as a target for the medical procedure as they are associated with the anatomy of interest that may or may not be visible to the imaging system throughout the entire procedure. Unlike the image of the anatomy of interest that may or may not remain visible in the GUI throughout the procedure, the one or more markers in the GUI can remain visible throughout the entire procedure.

In one or more embodiments, the present disclosure can provide a method for identifying and tracking target anatomy using on one or more imaging systems, such as an ultrasound imaging system, during a medical procedure for therapy delivery (e.g., an ablation procedure, a valve placement procedure, a lead placement procedure, a stent placement procedure, an LVAD placement procedure, etc.). The method can include a controller that can be adapted to receive image data from one or more imaging systems and use machine learning to identify an anatomical region of interest of the patient based on the medical procedure to be performed. The method can include using machine learning to identify the anatomy of interest based on the procedure of interest. Once the anatomy of interest is identified using machine learning or ultrasound, one or more markers (e.g., one or more point or plane markers) can be placed in the GUI by the controller to represent the target or landing zone of interest for the medical procedure. The one or more markers can represent the target or landing zone, which can be tracked in time and space and stay visible on the screen in the GUI, even if the actual anatomical image becomes obstructed or unavailable to the imaging system. The one or more point or plane markers can become the target for the medical procedure or therapy delivery as they are associated with the anatomy of interest that may or may not be visible to the imaging system throughout the procedure.

In one or more embodiments, the present disclosure provides a system and method for storing an image of the anatomy of interest and displaying the image in the GUI on the screen and overlaid with the live image even when the live image of one or more portions of the anatomy of interest becomes obstructed or unavailable. The method includes imaging a region of interest of the patient and saving the image data as reference data (e.g., echo images) taken prior to the instrument or medical device entry into the region of interest (e.g., a region of the heart). Once the instrument or medical device is introduced and guided to the region of interest, and the imaging of the area of interest of the patient becomes obstructed or unavailable, the earlier reference (clean) image of the same area of interest of the patient is overlaid and displayed by the controller in a semi-transparent fashion in the GUI using one or more common anatomical reference points (e.g., the coronary sinus and/or the aorta) between the live image and the stored reference image, thereby anchoring the two images together. The selection of common anatomical regions or features between the two images may be accomplished using image recognition techniques or software and/or machine learning. (e.g., utilizing image recognition/machine learning). The overlaying or merging of the live image with the reference image can be facilitated in real time, allowing for a phantom image to be displayed during live echo imaging, via ECG gating. The system and method can allow both the anatomy and the instrument or medical device to be viewed in the GUI simultaneously even if the live image of the anatomy becomes obstructed or unavailable. The system and method can allow both the anatomy of interest and the instrument or medical device to be viewed within the GUI without causing interference between each other. In other words, this approach can allow for merging or fusion of the reference image with the live image, providing improved visualization of the anatomy even in the presence of shadowing or reflection effects due to the instrument or medical device.

Further, in one or more embodiments, the system can be adapted to augment current echocardiography or other imaging techniques with targets, lines, markers, icons, or indicia to aid the clinician in implanting surgical instruments and devices within a patient. For example, for implantation of a mechanical circulatory support (MCS) device, placement of a sewing ring on a left ventricle (LV) apex is desirable for proper positioning of an inflow cannula of the device. In one or more embodiments, it may be useful for the clinician to register the sewing ring used to attach the device to the heart with one or more images provided by an ultrasound system. When the surgeon holds the sewing ring against the LV, the ultrasound image can show the patient's beating heart in real time, and the controller can be configured to automatically calculate the inflow cannula angle based on where the sewing ring is held and display the trajectory of the inflow cannula on the ultrasound image. In one or more embodiments, a feature can be displayed along with an augmented reality trajectory line to help interpret the data shown in the ultrasound image. For example, a green augmented marker can be overlaid on the ultrasound image to show a desired positioning of the sewing ring. Further, a red augmented marker can be overlaid on the ultrasound image to indicate that the sewing ring is not in the desired position. Once the sewing ring is in the desired position, the red augmented marker can transition to green.

In one or more embodiments, the GUI presented to the clinician can provide a roadmap for where to place implantation instruments and devices. For example, an augmented echocardiographic image can include targets or lines disposed onto real-time echocardiographic images for use during a procedure to aid with appropriate implant techniques and alignment of implant tools and devices. A trajectory line for an implant cannula for the MCS device implantation can be overlaid onto a real-time image. Further, one or more physiological landmarks of the region of the patient can be marked in the image for transcatheter mitral valve implantation or location for a transeptal puncture for atrial fibrillation (AF) procedures. In one or more embodiments, the augmented GUI presented to the clinician can include augmented markers that highlight the anatomical or physiological landmarks within the target region of a patient. In one or more embodiments, the augmented GUI provided to the clinician can include augmented markers that highlight the position, orientation, and trajectory of a surgical instrument as the instrument is being utilized within the patient. One or more sensors can be disposed on the instrument such that the instrument can be tracked utilizing, e.g., an electromagnetic (EM) tracking system. Additionally, depending upon a cut plane of the echocardiographic image, the instrument may be visible in one or more views but not in others, and the instrument may be sliced/imaged through the middle of the shaft rather than the tip, causing confusion as to whether the tip is in a ventricle or an atrium. For example, if a view of the instrument is in a plane that cuts across a portion of the ventricle, the tip will appear to be there, but the tip may instead be in the atrium. By overlaying an augmented image of the instrument onto a real-time plane of ultrasound image data, the actual location of the instrument can be seen by the clinician.

Any suitable system or systems can be utilized with the embodiments of the present disclosure, e.g., the systems described in U.S. Patent Publication No. 2017/0135760 to Girotto et al., entitled SYSTEMS AND METHODS FOR ULTRASOUND IMAGE-GUIDED ABLATION ANTENNA PLACEMENT; and U.S. Pat. No. 8,401,616 to Verard et al., entitled NAVIGATION SYSTEM FOR CARDIAC THERAPIES.

FIG. 1 is a schematic perspective view of one embodiment of a treatment system 10, which includes a computing device 100, a display 110, a table 120, an instrument 130, an ultrasound imager 140, and an ultrasound workstation 150. Computing device 100 may be, for example, a laptop computer, desktop computer, tablet computer, smart phone, or other similar device. Computing device 100 may be configured to control an electrosurgical generator, a peristaltic pump, a power supply, and/or any other accessories and peripheral devices relating to, or forming part of, system 10. Display 110 is configured to output instructions, images, and messages relating to at least one of a performance, position, orientation, or trajectory of the instrument 130. Further, the display 110 can be configured to output information regarding the instrument 130, e.g., model number, type, size, etc. Table 120 may be, for example, an operating table or other table suitable for use during a surgical procedure that includes an electromagnetic (EM) field generator 121. EM field generator 121 is used to generate an EM field during the procedure and forms part of an EM tracking system that is used to track the positions of one or more surgical instruments within the body of a patient. EM field generator 121 may include various components, such as a specially designed pad to be placed under, or integrated into, an operating table or patient bed. An example of such an EM tracking system is the AURORA™ system sold by Northern Digital Inc. While the present disclosure describes the use of system 10 in a surgical environment, it is also envisioned that some or all of the components of system 10 may be used in alternative settings, for example, an imaging laboratory and/or an office setting.

In addition to the EM tracking system, the instrument 130 may also be visualized by using ultrasound imaging. Ultrasound imager 140, such as an ultrasound wand, may be used to image the patient's body during the procedure to visualize the location of the surgical instruments, such as instrument 130, inside the patient's body. Ultrasound imager 140 may have an EM tracking sensor embedded within or attached to the ultrasound wand, for example, a clip-on sensor, or a sticker sensor. As described further herein, ultrasound imager 140 may be positioned in relation to instrument 130 such that the instrument is at an angle to the ultrasound image plane, thereby enabling the clinician to visualize the spatial relationship of the instrument with the ultrasound image plane and with objects being imaged. Further, the EM tracking system may also track the location of ultrasound imager 140. In one or more embodiments, one or more ultrasound sensors 140 may be placed inside the body of the patient. The EM tracking system may then track the location of such ultrasound sensors 140 and the instrument 130 inside the body of the patient.

The location of the instrument 130 within the body of the patient may be tracked during the surgical procedure. An exemplary method of tracking the location of the instrument 130 includes using the EM tracking system, which tracks the location of the instrument by tracking sensors attached to or incorporated in the instrument. Various types of sensors may be used, such as a printed sensor, the construction and use of which is more fully described in co-pending U.S. Patent Publication No. 2016/0174873, entitled MEDICAL INSTRUMENT WITH SENSOR FOR USE IN A SYSTEM AND METHOD FOR ELECTROMAGNETIC NAVIGATION. Prior to starting the procedure, the clinician can verify the accuracy of the tracking system using any suitable technique or techniques.

Any suitable instrument or device 130 can be utilized with the system 10, e.g., one or more implantable devices, implant delivery devices, therapy delivery devices, surgical devices, mechanical circulatory support (e.g. LVAD) devices, coronary stent devices, heart valve devices, heart valve repair devices, cardiac ablation devices, cardiac lead devices, drug delivery devices, catheter delivery devices, and endoscopic delivery devices.

Figure 2:
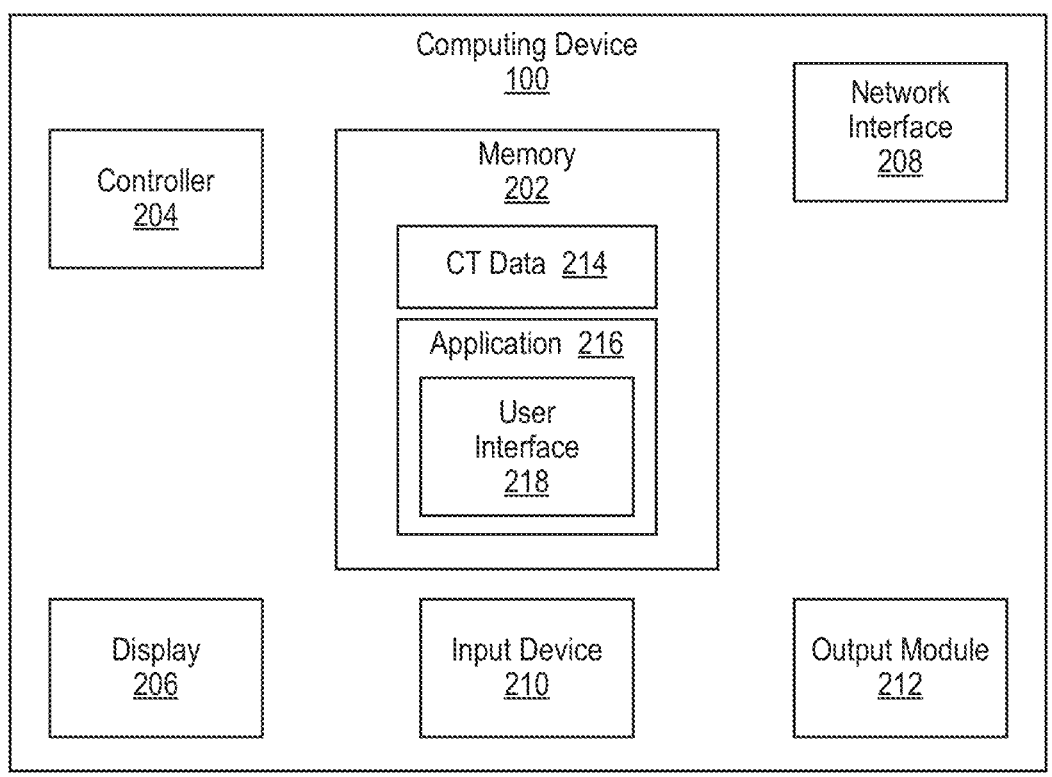
FIG. 2 is a schematic view of one embodiment of a computer device of the system of FIG. 1.

FIG. 2 is a schematic view of one embodiment of the computing device 100 of FIG. 1. Computing device 100 can include memory 202, controller or processor 204, display 206, network interface 208, input device 210, and/or output module 212.

Memory 202 includes any non-transitory computer-readable storage media for storing data and/or software that is executable by controller 204 and that controls the operation of computing device 100. In one or more embodiments, memory 202 can include one or more solid-state storage devices such as flash memory chips. In one or more embodiments, memory 202 may include one or more mass storage devices connected to the controller 204 through a mass storage controller (not shown) and a communications bus (not shown). Although the description of computer-readable media herein refers to a solid-state storage, it should be appreciated by those skilled in the art that computer-readable storage media can be any available media that can be accessed by the controller 204. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium that can be used to store the desired information and that can be accessed by computing device 100. In one or more embodiments, computer-readable storage media can be stored in the cloud or remote storage and accessed using any suitable technique or techniques through at least one of a wired or wireless connection.

Memory 202 may store at least one of application 216 or image data 214 such as reference image data. Application 216 may, when executed by controller 204, cause display 206 to present user interface 218.

Controller 204 may be a general-purpose controller, a specialized graphics processing unit (GPU) adapted to perform specific graphics processing tasks while freeing up the general-purpose controller to perform other tasks, and/or any number or combination of such controllers.

Display 206 may be touch sensitive and/or voice activated, enabling display 206 to serve as both an input and output device. Alternatively, a keyboard (not shown), mouse (not shown), or other data input devices may be employed.

Network interface 208 may be adapted to connect to a network such as a local area network (LAN) that includes a wired network and/or a wireless network, a wide area network (WAN), a wireless mobile network, a Bluetooth network, and/or the internet. For example, computing device 100 may receive computed tomographic (CT) image data and/or one or more other types of image data of a patient from a server, for example, a hospital server, internet server, or other similar servers, for use during the procedure. Patient CT image data or other image data may also be provided to computing device 100 via a removable memory 202. Reference image data such as a reference ultrasound image may also be provided to computing device 100 from an imaging system prior to the medical procedure. Computing device 100 may receive updates to its software, for example, application 216, via network interface 208. Computing device 100 may also display notifications on display 206 that a software update is available.

Input device 210 may be any device that enables a user to interact with computing device 100, such as, for example, a mouse, keyboard, foot pedal, touch screen, augmented-reality input device such as hand gestures or body movements, and/or voice interface.

Output module 212 may include any connectivity port or bus, such as, for example, parallel ports, serial ports, universal serial busses (USB), or any other similar connectivity port known to those skilled in the art.

Application 216 may be one or more software programs stored in memory 202 and executed by controller 204 of computing device 100. As will be described in more detail herein, during the planning phase, application 216 guides a clinician or physician through a series of steps to identify a target, size the target, size a treatment zone, and/or determine an access route to the target for later use during the procedure phase. In one or more embodiments, application 216 is loaded on computing devices in an operating room or other facility where surgical procedures are performed, and is used as a plan or map to guide a clinician performing a surgical procedure, but without any feedback from the instrument 130 used in the procedure to indicate where the instrument 130 is located in relation to the plan. In one or more embodiments, system 10 provides computing device 100 with data regarding the location of the instrument 130 within the body of the patient, such as by EM tracking, which application 216 may then use to indicate on the plan where the instruments are located. In one or more embodiments, the system 10 can provide computing device 100 with data regarding the location of two or more instruments 130 within the body of the patient.

Application 216 may be installed directly on computing device 100, or may be installed on another computer, for example a central server, and opened on computing device 100 via network interface 208. Application 216 may run natively on computing device 100, as a web-based application, or any other format known to those skilled in the art. In one or more embodiments, application 216 will be a single software program having all of the features and functionality described in the present disclosure. In one or more embodiments, application 216 may be two or more distinct software programs providing various parts of these features and functionality. For example, application 216 may include one software program for use during the planning phase and a second software program for use during the procedure phase. In one or more embodiments, application 216 can include different programs for different types of treatments. In such instances, the various software programs forming part of application 216 may be enabled to communicate with each other and/or import and export various settings and parameters relating to the treatment and/or the patient to share information. For example, a treatment plan and any of its components generated by one software program during the planning phase may be stored and exported to be used by a second software program during the procedure phase.

Application 216 communicates with a user interface 218, which generates a user interface for presenting visual interactive features to a clinician, for example, on display 206 and for receiving clinician input, for example, via a user input device. For example, user interface 218 may generate a graphical user interface (GUI) and output the GUI to display 206 for viewing by a clinician. Examples of the GUI are described herein with reference to FIGS. 3A-3E, 4, and 8-9.

Computing device 100 is linked to display 110, thus enabling computing device 100 to control the output on display 110 along with the output on display 206. Computing device 100 may control display 110 to display output that is the same as or similar to the output displayed on display 206. For example, the output on display 206 may be mirrored on display 110. In one or more embodiments, computing device 100 may control display 110 to display different output from that displayed on display 206. For example, display 110 may be controlled to display guidance images and information during the surgical procedure, while display 206 is controlled to display other output, such as configuration or status information.

As used herein, the term "clinician" refers to any medical professional (i.e., doctor, surgeon, nurse, or the like) or other user of the treatment system 10 involved in planning, performing, monitoring, and/or supervising a medical procedure involving the use of the embodiments described herein.

Figure 3A:
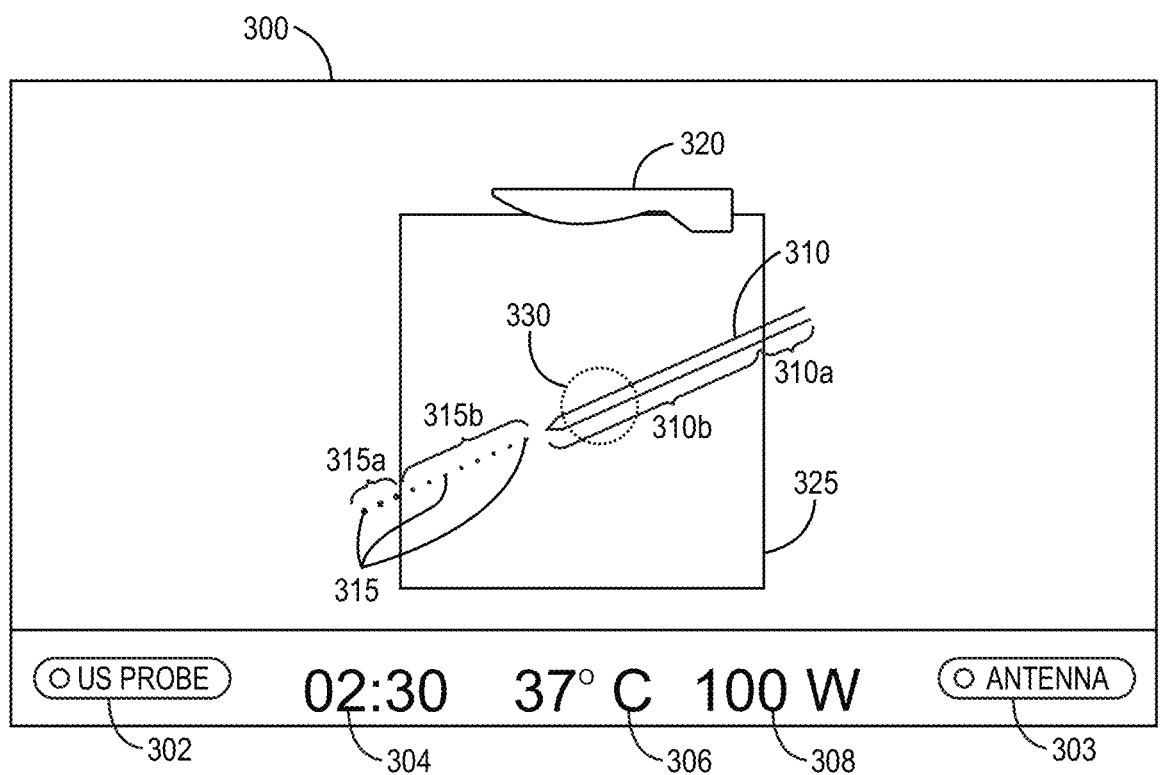
FIG. 3A is a schematic view of one embodiment of a graphical user interface provided by the system of FIG. 1.

FIG. 3A is a schematic view of a GUI 300 generated by user interface 218 that may be presented by computing device 100 on display 206 and/or display 110. GUI 300 includes graphical representation of an antenna 310 corresponding to instrument 130, a graphical representation of an ultrasound wand 320 corresponding to ultrasound imager 140, a graphical representation of a trajectory 315 of the instrument, an ultrasound image plane 325, and a projected region of interest of the patient 330 showing a projected region as configured for the current procedure. Ultrasound image plane 325 can include an ultrasound image (not shown here for the purpose of more clearly depicting the elements being described) based on ultrasound image data captured by ultrasound imager 140. GUI 300 can further include a probe indicator 302 and antenna indicator 303 that indicates whether ultrasound imager 140 and the instrument 130 are connected to computing device 100 and system 10. GUI 300 can also include other indicators of time 304, temperature 306, and wattage 308 or other information related to the procedure, e.g., temperature and wattage of an instrument. In one or more embodiments, GUI 300 can further include information regarding the instrument 130, e.g., model, type, dimensions, etc.

Trajectory 315 shows the trajectory at which the instrument 130 is being navigated inside the patient's body. In one or more embodiments, the length of trajectory 315 corresponds to the length of the instrument 130. In one or more embodiments, the trajectory of the instrument shown in the graphical user interface has at least one of a length or width approximately equal to a respective length and width of the instrument. As used herein, the term "approximately equal" means that at least one of the length or width of the trajectory as shown in the GUI is no greater than or less than 1 cm of the respective length or width of the instrument 130. Thus, when positioning the instrument 130 and ultrasound imager 140 outside the patient's body, trajectory 315 will show the distance the instrument 130 can be navigated into the patient's body. As such, the clinician can determine whether the instrument 130 can reach the target region inside the patient's body before inserting the instrument into the patient's body.

In one or more embodiments, GUI 300 may depict antenna 310 of instrument 130 and at least one of its position, orientation, or trajectory 315 of the instrument as outlines such that the ultrasound image displayed on ultrasound image plane 325 is not obscured by such outlines. GUI 300 further shows the antenna 310 of instrument 130 and at least one of its position, orientation, or trajectory 315 in relation to a plane of the ultrasound image data, i.e., the ultrasound image plane 325. In one or more embodiments, the controller 204 is further adapted to determine an intersection between the instrument 130 and the plane of the ultrasound image data 325 and display an indicator of the intersection between the instrument and the plane of the ultrasound image data in the GUI 400. For example, when the instrument 130 does not intersect ultrasound image plane 325, the antenna 310 can be depicted as shadowed (e.g. dimmed or greyed-out). For example, as shown in FIG. 3A, the antenna 310 is depicted in a shadowed section 310b for the portion of the antenna displayed behind ultrasound image plane 325. Likewise, trajectory 315 is depicted as a shadowed section 315b for the portion of trajectory 315 that is behind ultrasound image plane 325. In contrast, the portion of the trajectory 315a that is in front of ultrasound image plane 325 is shown as regular or solid image (of normal brightness and not shadowed or dimmed). In one or more embodiments, one or more colors can be utilized to depict the shadowed section 315b, and one or more differing colors can be utilized to depict the trajectory 315. Further, in one or more embodiments, the shadowed section 315b can be depicted in dashed lines and the trajectory 315 can be depicted in solid lines.

Figure 3B:
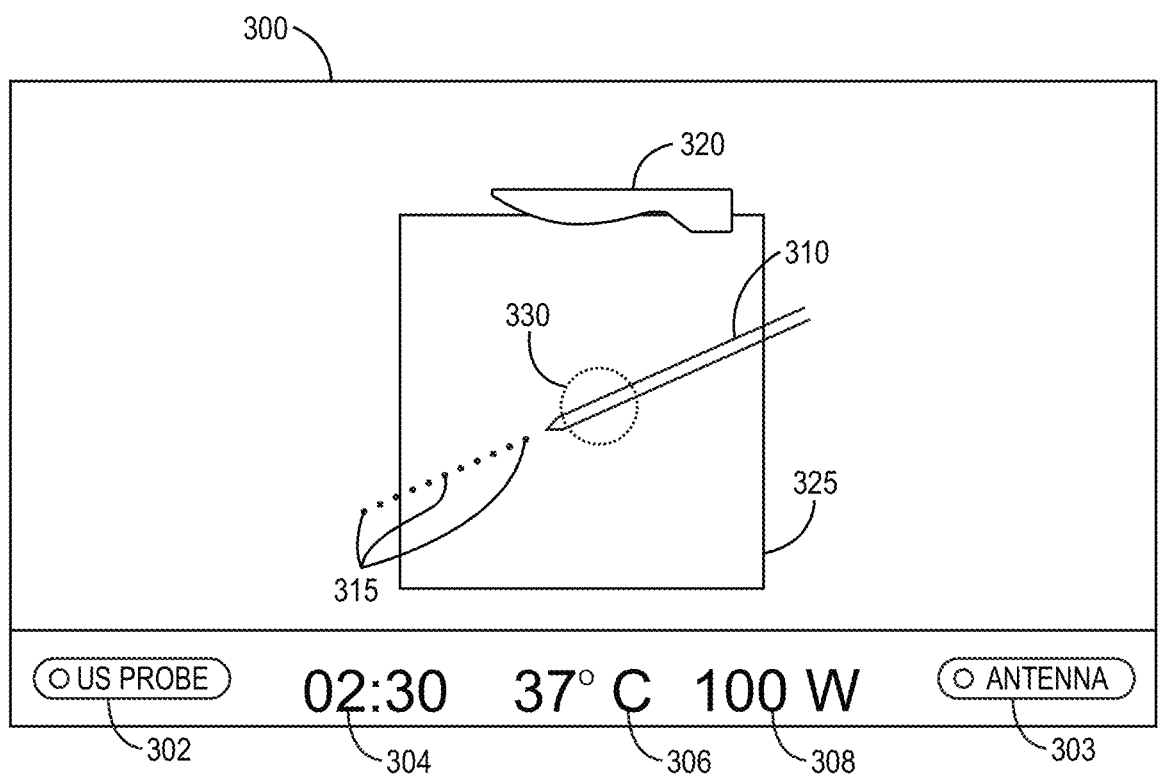
FIG. 3B is a schematic view of another embodiment of a graphical user interface provided by the system of FIG. 1.

While FIG. 3A shows an example where all of the antenna 310 and trajectory 315 are behind ultrasound image plane 325, FIG. 3B shows an example where all of the antenna and trajectory are in front of ultrasound image plane 325. That is, the instrument 130 is located entirely in front of, and does not intersect, the plane of the image 325 generated by ultrasound imager 140.

Figure 3C:
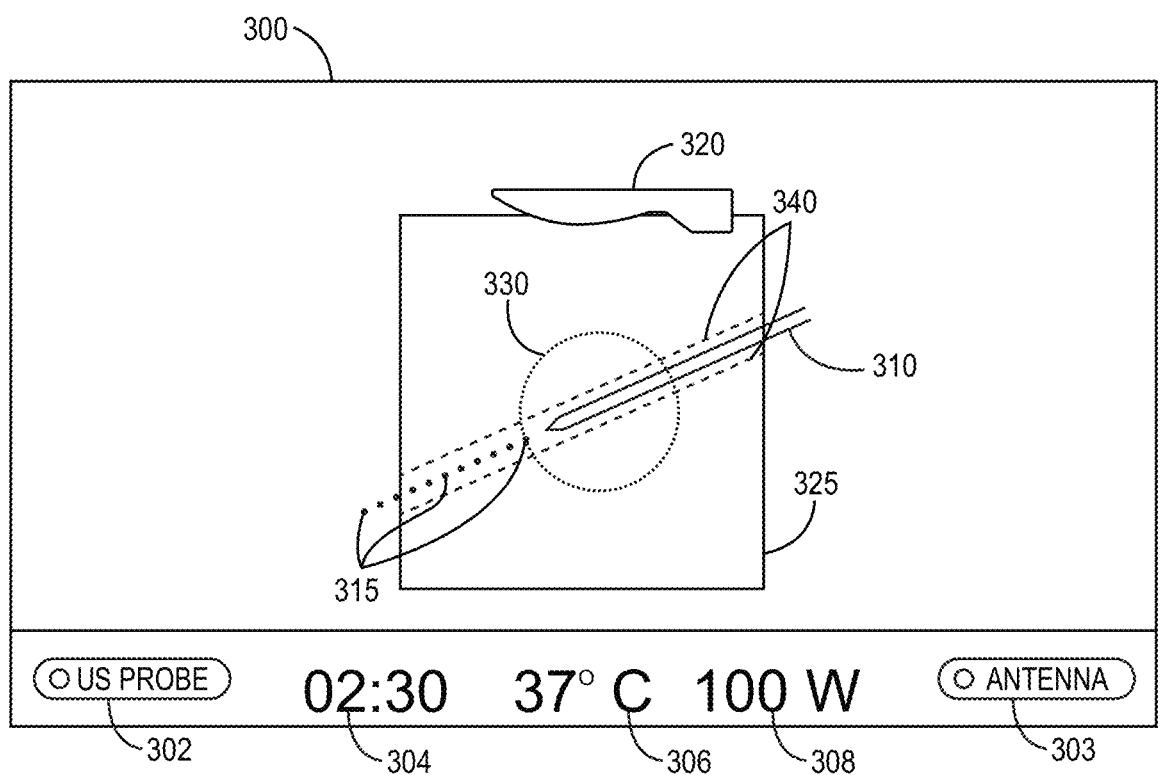
FIG. 3C is a schematic view of another embodiment of a graphical user interface provided by the system of FIG. 1.

FIG. 3C shows another example GUI 300 generated by user interface 218 that may be displayed by computing device 100 on display 206 and/or display 110. FIG. 3C includes many of the same elements as FIGS. 3A and 3B. Those elements are identified using the same reference numerals as in FIGS. 3A and 3B and will not be described again for purpose of brevity.

FIG. 3C shows an example where the antenna 310 of instrument 130 is co-planar with ultrasound image plane 325. The area of intersection between a plane of the antenna 310 and ultrasound image plane 325 is indicated by an obround 340. Because antenna 310 is co-planar with ultrasound image plane 325, obround 340 is shown as two parallel lines on either side of the antenna 310 and trajectory 315.

Figure 3D:
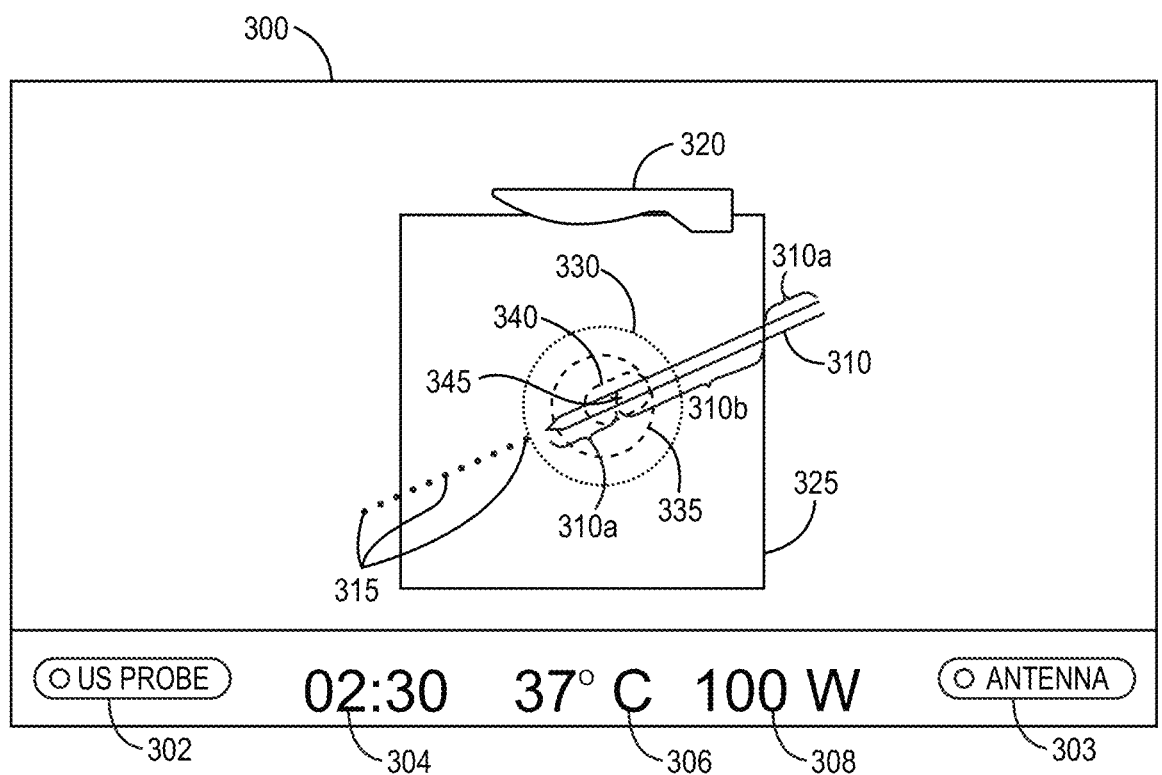
FIG. 3D is a schematic view of another embodiment of a graphical user interface provided by the system of FIG. 1.

FIG. 3D shows another embodiment of GUI 300, where the antenna 310 of instrument 130 intersects ultrasound image plane 325. Unlike in FIG. 3C, where the antenna 310 is co-planar with ultrasound image plane 325 and obround 340 extends the length of antenna 310 and trajectory 315, in FIG. 3D, obround 340 appears elliptical around the area of intersection between the antenna and ultrasound image plane. The length and position of obround 340 is determined by the angle of intersection between the antenna 310 and ultrasound image plane 325. That is, obround 340 shows the direction and acuteness of the angle of intersection between the antenna 310 and ultrasound image plane 325. The point of intersection between the antenna 310 and ultrasound image plane 325 is shown by intersection indicator 345.

GUI 300 may further show a progress indicator 335 after computing device 100 determines that the procedure has been started. The progress indicator 335 can show the progress of the procedure being performed. The progress indicator 335 will start close to the antenna 310 and move out toward projected zone indicator 330 as the procedure proceeds. The progress indicator 335 can be depicted using any suitable images or indicia, e.g., color, line thickness, brightness, etc.

Figure 3E:
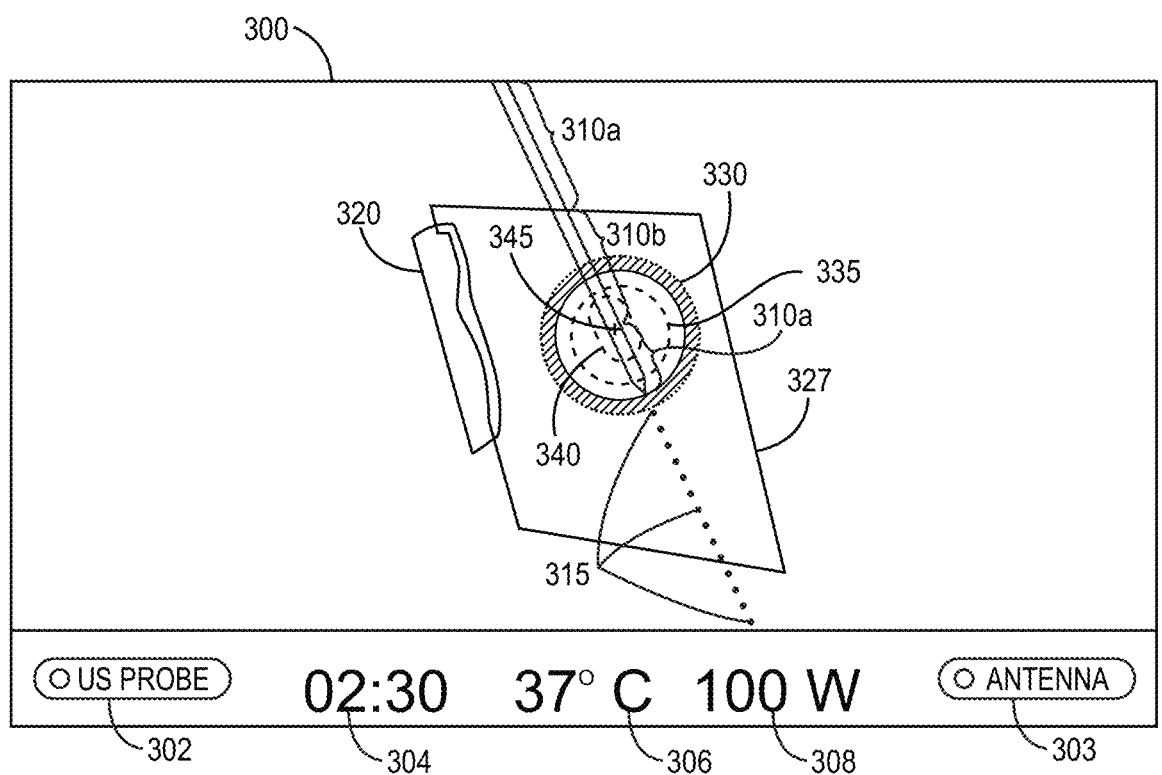
FIG. 3E is a schematic view of another embodiment of a graphical user interface provided by the system of FIG. 1.

FIG. 3E shows another embodiment of GUI 300 generated by user interface 218 that may be displayed by computing device 100 on display 206 and/or display 110. FIG. 3E includes many of the same elements as FIGS. 3A-3D. Those elements are identified using the same reference numerals as in FIGS. 3A-3D and will not be described again for purpose of brevity.

FIGS. 3A-3D show ultrasound image plane 325 in which the orientation of ultrasound wand 320 and ultrasound image plane 325 are maintained in a fixed orientation normal to GUI 300. FIG. 3E, in contrast, depicts ultrasound wand 320 and an ultrasound image plane 327 according to an orientation of ultrasound imager 140 within an EM field generated by EM field generator 121. Thus, when the clinician moves ultrasound imager 140, the depiction of ultrasound wand 320 and ultrasound image plane 327 in GUI 300 changes according to the movement and angle of ultrasound imager 140 within the EM field, thereby providing a perspective view of the target region or zone and the position of the instrument 130 therein.

GUI 300 may further include a perspective view area configured to correspond to a portion of the EM field that includes the treatment region or target zone. For example, the patient may be positioned on table 120 such that the EM field generated by EM field generator 121 includes the target zone. Computing device 100 may then automatically and/or with assistance from the clinician select a portion of the EM field that includes the target zone, and may configure application 216 and/or GUI 300 to depict the antenna 310, ultrasound wand 320, ultrasound image plane 327, and the various other elements described herein in the perspective view area based on their detected and/or determined positions within the EM field. For example, ultrasound image plane 327 and ultrasound wand 320 may only be depicted in the perspective view area when ultrasound imager 140 is detected to be positioned within the portion of the EM field that is configured to be displayed in the perspective view area of GUI 300. Likewise, the antenna 310 may only be depicted in the perspective view area when the instrument 130 is detected to be positioned within the portion of the EM field that is configured to be displayed in the perspective view area of GUI 300. Thus, when ultrasound imager 140 and/or the instrument 130 are not in the portion of the EM field that is configured to be displayed in the perspective view area of GUI 300, GUI 300 will not display ultrasound wand 320, ultrasound image plane 327, and/or antenna 310 in the perspective view area. The portion of the EM field that is configured to be displayed in the perspective view area of GUI 300 may be adjusted during the procedure, such as by moving and/or zooming in and out.

As depicted in FIG. 3E, ultrasound imager 140 is rotated approximately 90° to the left and obliquely to the plane of the portion of the EM field shown in the perspective view area of GUI 300. These differences in orientation assist the clinician in understanding how movement of ultrasound imager 140 affects both ultrasound image plane 327 and ultrasound image plane 325. As depicted in FIG. 3E, projected zone indicator 330 and/or progress indicator 335 may be three-dimensional (3D) projections. This 3D projection of either projected zone indicator 330 and/or progress indicator 335 provides greater understanding of how the target zone interacts with all tissue and other structures in the zone during treatment. Further, these features allow the clinician to sweep across the instrument 130 to ascertain with greater clarity the effects of the treatment on the treatment zone.

Figure 4:
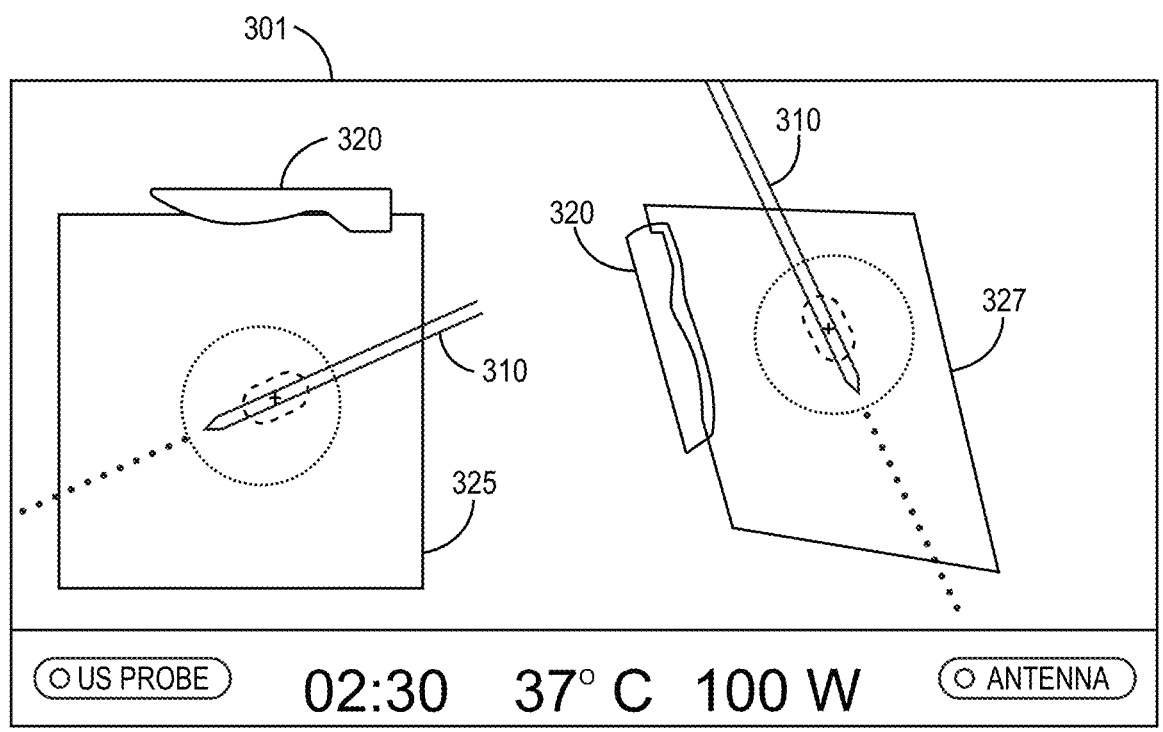
FIG. 4 is a schematic view of another embodiment of a graphical user interface provided by the system of FIG. 1.

FIG. 4 shows another embodiment of a GUI 301 generated by user interface 218 that may be displayed by computing device 100 on display 206 and/or display 110. FIG. 4 includes many of the same elements as FIGS. 3A-3E. Those elements are identified using the same reference numerals as in FIGS. 3A-3E and will not be described again for purpose of brevity.

GUI 301 includes side-by-side depictions of ultrasound image plane 325, which is displayed normal to GUI 300, as shown in FIGS. 3A-3D, and ultrasound image plane 327, which is shown relative to the placement of ultrasound imager 140 within the EM field generated by EM field generator 121.

In one or more embodiments, the controller 204 of the computing device 100 of system 10 can be adapted to also identify one or more physiological landmarks within the region of the patient and generate one or more markers, icons, or indicia in the GUI 300 that augments these one or more physiological landmarks so that the clinician can more readily identify them during the procedure. In one or more embodiments, the physiological landmark of the region of the patient can include any suitable structure or portion of the patient's physiology, one or more portions of the heart including, for example, one or more valves or portions thereof, one or more chambers or portions thereof, the apex or portions thereof, the septum or portions thereof, one or more vessels leading to or from the heart including, for example, the aorta or portions thereof, the pulmonary artery or portions thereof, the pulmonary vein or portions thereof, the superior vena cava or portions thereof, or the inferior vena cava or portions thereof_Further, in one or more embodiments, the graphical user interface 300 includes at least one marker representative of the physiological landmark. In one or more embodiments, the controller 204 is adapted to attach these markers to the physiological landmarks such that the markers are dynamic. In other words, the markers are attached to the physiological landmarks such that the markers move in registration with the landmarks in the GUI 300. Such registration of the markers with the physiological landmarks can aid the clinician in guiding the instrument 130 and/or one or more devices to the target region of the patient even though the patient or the region is moving in connection, e.g., with inhalation and exhalation and/or the beating of a heart of the patient.

In one or more embodiments, the controller 204 of the computing device 100 of system 10, upon execution of application 216, can be adapted to use machine learning or artificial intelligence (AI) to identify one or more physiological landmarks within the region of the patient and generate one or more markers, icons, and indicia in the GUI 300 that augments these one or more physiological landmarks so that the clinician can more readily identify them during the procedure. In one or more embodiments, application 216 includes one or more machine learning algorithms to identify one or more physiological landmarks within the region of the patient and/or to provide an optimum trajectory for guiding a surgical instrument and/or medical device through a region of a patient based on data acquired during the procedure and/or data acquired prior to the procedure. The machine learning algorithms can also adjust the trajectory as the procedure advances. For example, one or more algorithms can form a wider trajectory line in the GUI 300 if there is a large target zone for treatment or it can adjust the trajectory angle once anchored (e.g., the algorithm starts with the trajectory point for entry into the heart but then adjusts the trajectory once that access anchor point is established).

Figure 5:
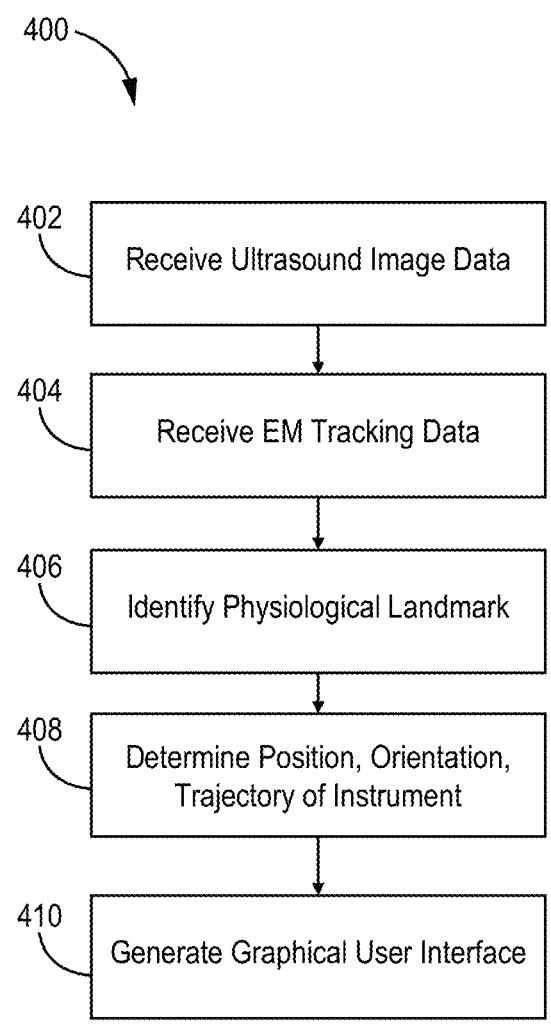
FIG. 5 is a flowchart of one embodiment of a method of guiding an instrument through a region of a patient utilizing the system of FIG. 1.

Any suitable technique or techniques can be utilized with the system 10 for guiding an instrument through a region of a patient. For example, FIG. 5 is a flowchart of one method 400 for guiding the instrument 130 through a region of a patient. Although described in reference to system 10 of FIGS. 1-4, the method 400 can be utilized with any suitable system. In one or more embodiments, the controller 204 can be adapted to utilize the method 400. Prior to beginning the procedure, any suitable settings may be entered manually by a clinician as user input data or may be preloaded from a preconfigured configuration settings file that was previously entered by the clinician. The settings may be based on a particular treatment profile specific to the patient and/or the type of procedure to be performed. Once received, GUI 300 can display these settings as indicators 304, 306, and 308, respectively.

At 402, ultrasound image data can be received from the ultrasound sensor or imager 140 by the computing device 100. The ultrasound image data may be relayed from ultrasound workstation 150. Next, or concurrently with step 402, computing device 100 receives EM tracking data from the EM tracking system for ultrasound imager 140 and the instrument 130 at 404. The EM tracking data is representative of positions and orientations of each of the ultrasound sensor and the instrument 130 relative to the region of the patient.

At 406, one or more physiological landmarks based on the ultrasound image data can be identified either by the clinician or the controller 204 using any suitable technique or techniques. Computing device 100 can determine at least one of a position, orientation, or trajectory of the instrument 130 based on the EM tracking data at 408 using any suitable technique or techniques. The computing device 100 can also determine an intersection between the instrument 130, or the trajectory of the instrument, and the plane of the ultrasound image data received from ultrasound imager 140.

At 410, the controller 204 of the computing device 100 can generate a GUI 300 showing at least one of a position, orientation, or trajectory of the instrument 130 relative to the plane 325 of the ultrasound image data, which is based on the ultrasound image data received from ultrasound imager 140, and a target zone that is registered with the one or more physiological landmarks identified at 406. Any suitable technique or techniques can be utilized to show the target zone. In one or more embodiments, the controller 204 can be adapted to determine the target zone based on user input data and generate the target zone in the GUI based upon the user input data. The computing device 100 can display the GUI 300 on display 206 and/or display 110.

In one or more embodiments, the controller 204 can be adapted to determine whether at least one of the position, orientation, or trajectory of the instrument 130 has changed. If yes, then the controller 204 can be adapted to generate an updated graphical user interface showing at least one of an updated position, orientation, or trajectory of the instrument. These steps may be performed interchangeably and/or concurrently and can be performed iteratively throughout the procedure.

The method 400 can further include determining whether at least one of a position or orientation of the ultrasound sensor has changed and generating an updated graphical user interface 300 showing an updated plane of the ultrasound image data 325 if it is determined that at least one of the position or orientation of the ultrasound sensor has changed. Any suitable technique or techniques can be utilized to generate an updated graphical user interface 300 if the position or orientation of the ultrasound sensor has changed.

In one or more embodiments, after updating the GUI 300, computing device 100 can determine whether the procedure is complete. If yes, processing ends. If not, computing device 100 continues to display the GUI 300.

In one or more embodiments, the computing device 100 can determine whether the procedure has started. If yes, computing device 100 can update the GUI 300 with an indicator of the progress of the procedure, for example, indicator 335 shown in FIGS. 3D and 3E. Thereafter, the computing device 100 can determine whether the procedure has been completed. If yes, processing ends. If not, the GUI 300 is iteratively updated based on the progress of the procedure.

The controller 130 can further be adapted to receive a reference ultrasound image of the region of the patient when the instrument is located outside of the region, register the reference ultrasound image with the physiological landmark, and overlay the registered reference ultrasound image with the graphical user interface. Any suitable technique or techniques can be utilized to overlay the registered reference ultrasound image with the graphical user interface.

Figure 6:
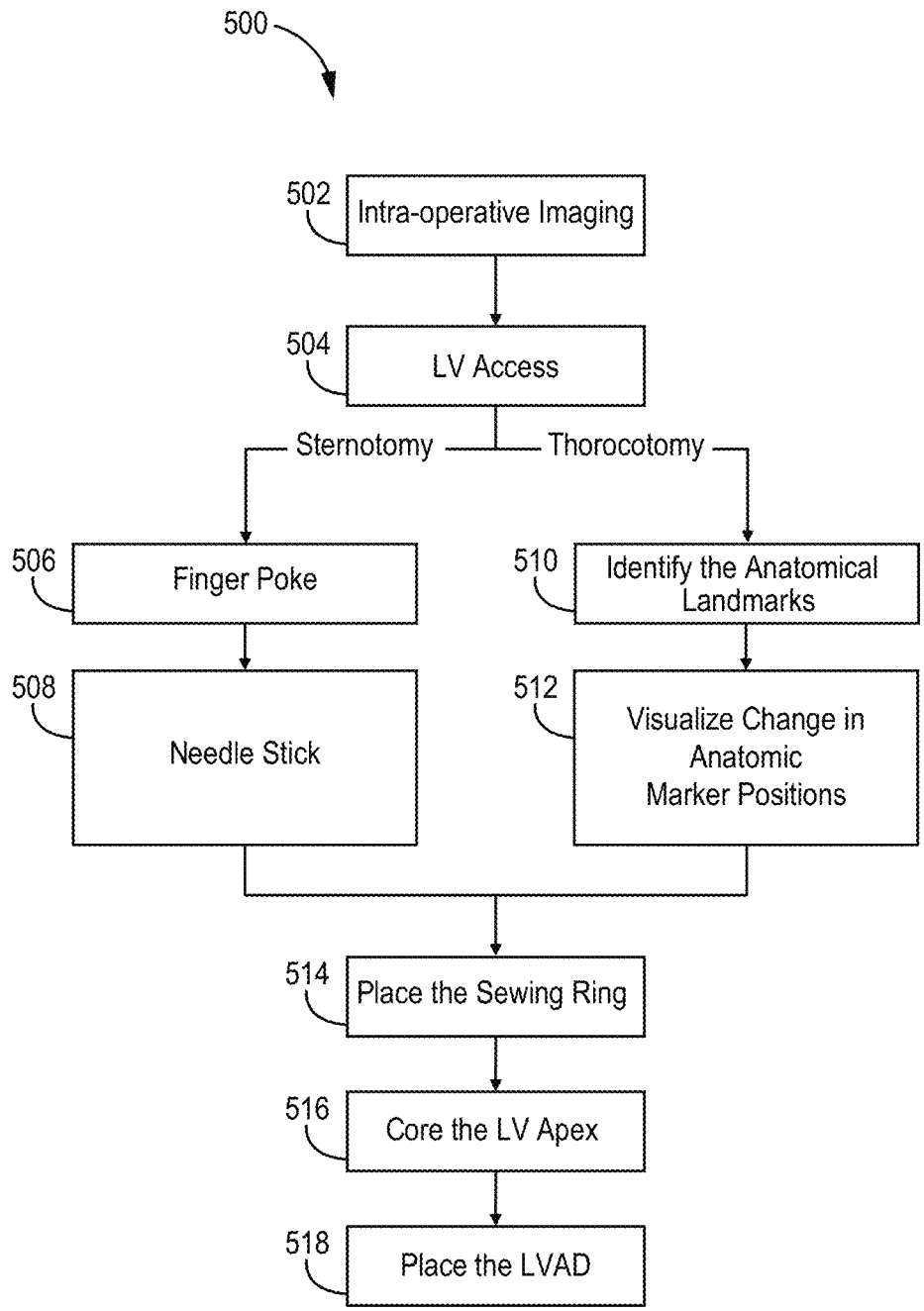
FIG. 6 is a flowchart of one embodiment of a method of implanting an LVAD device utilizing the system of FIG. 1.

The systems and methods described herein can be utilized for any procedure or treatment. For example, in one or more embodiments, the system 10 can be utilized for implantation of a left ventricular assist device (LVAD). FIG. 6 is a flowchart of one embodiment of a method 500 of utilizing the system 100 to implant an LVAD. Although described in reference to the system 10 of FIGS. 1-4, the method 500 can be utilized with any suitable system. In one or more embodiments, the controller 204 can be adapted to utilize the method 500 of FIG. 6.

A target region within the patient can be imaged at 502 using any suitable technique or techniques, e.g., echocardiography. Any suitable echocardiography techniques can be utilized, e.g., transesophageal echocardiography (TEE). A view of the intraventricular septum and mitral valve location can be imaged using the imaging system 10. In one or more embodiments, physiological landmarks such as the mitral valve, IV septum, LV apex, aortic valve, etc., can be identified by the system 10 using any suitable technique.

Access to the LV at 504 can be gained with the instrument 130 using any suitable technique, e.g., through a sternotomy or a thoracotomy. For a sternotomy, a finger poke at 506 where the clinician's finger pushes against the myocardium to define the LV apex by viewing the echocardiography image and identifying the indent relative to the geometry of the heart can be performed. In one or more embodiments, this step may not be required as the clinician can be presented with the augmented image of the instrument 130 and physiological markers in the GUI 300. In one or more embodiments, the deformation caused by the finger poke can be augmented in the GUI 300 and indicated with a marker or indicia and connected to a marker that is connected to the LV apex landmark identified by the system 10 or the clinician. Following identification of the LV apex, a needle can be inserted into the apex at 508 and viewed on the echocardiograph image so that the needle is parallel to the septum and the needle trajectory is toward the mitral valve and not angled toward the aortic valve. Once again, this step may be eliminated by tracking the needle (e.g., instrument 130) and providing the user with an augmented image of the needle in the GUI 300. In one or more embodiments, one or more sensors can be connected to the needle such that the needle can be tracked using any suitable system, e.g., the EM tracking system.

For a thoracotomy, physiological landmarks can be identified at 510 by direct visualization through an incision by lifting the heart to the incision and identifying the vasculature to determine where the apex is located. In one or more embodiments, augmented markers indicating various physiological landmarks can be dynamically connected to the landmarks in the GUI 300. Such markers can be registered with the physiological landmarks following heart elevation with the heart in the new position to help with the LV placement. In one or more embodiments, new markers can be provided for various physiological landmarks, and the changes between the preprocedural imaging markers and post heart elevation can be augmented in the GUI 300 at 512. Further, in one or more embodiments, a trajectory for the instrument 130 for implantation can be provided for both the normal vs. elevated positions of the heart.

Following identification of the apex, a sewing ring can be disposed on the patient's heart at 514 using any suitable technique. Currently, some clinicians utilize a tissue marking pen to mark where the sewing ring will be placed on the LV apex, and the sewing ring can then be sutured to the heart at that location. In one or more embodiments, the EM system can be utilized to track the instrument 130 that will be utilized to place the sewing ring to track at least one of a position, orientation, or trajectory of the instrument. An augmented image of the instrument 130 can be added to the GUI 300 as well as an augmented image of the sewing ring. For example, one or more sensors can be added to the sewing ring such that the location of the sewing ring can be determined by the EM system.

Figure 8:
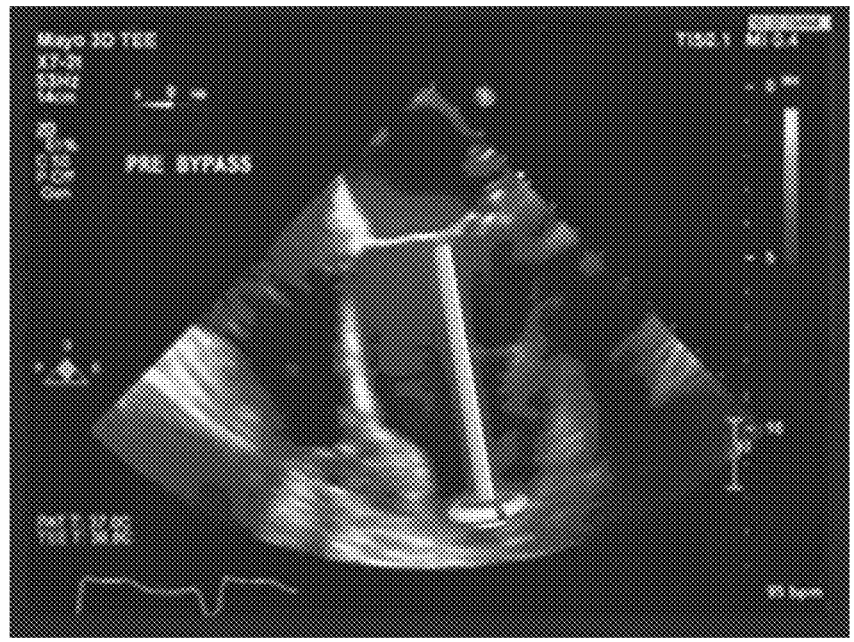
FIG. 8 is a schematic view of another embodiment of a graphical user interface.

A trajectory for the instrument 130 can be evaluated relative to marker lines of the IV septum and mitral valve added to the GUI 300 to ensure proper placement (parallel to IV septum, perpendicular to the MV). Any suitable technique can be utilized to determine the proper trajectory. For example, FIG. 8 is a schematic view of a GUI 702 with an augmented image of the sewing ring and a projected trajectory. Further, the trajectory can be evaluated in multiple views in the GUI 702, e.g., cross-sectional, longitudinal, three-dimensional. In one or more embodiments, the proper trajectory can change color in the GUI 702 (or provide guideline lanes that indicate boundaries within which the instrument 130 is to be disposed) as the ring is manipulated on the surface of the heart (e.g., red indicates an incorrect placement, green indicates a desired placement, dashed line transitioning to solid line indicates desired placement, brightness of line or text that indicate desired placement). In one or more embodiments, the controller 204 can be adapted to measure one or more distances and angles between augmented markers and the trajectory of the instrument 130 and provide such distances to the clinician in the GUI 702 (e.g., a distance between the IV septum and a trajectory line of the instrument toward the apex and basal portion of heart, a distance between IV septum and the instrument trajectory, a distance between the free wall and instrument trajectory, etc.).

In one or more embodiments, the sewing ring can include a gimble that allows a desired number of degrees of freedom of an angle of the sewing ring relative to the epicardium of the heart after the ring is sutured to the heart. The augmented trajectory and visualization of the sewing ring in the GUI 702 can aid with optimizing placement angle of the gimble.

Following attachment of the sewing ring, the LVAD can be connected to the sewing ring at 518 using any suitable technique or techniques.

Figure 7:
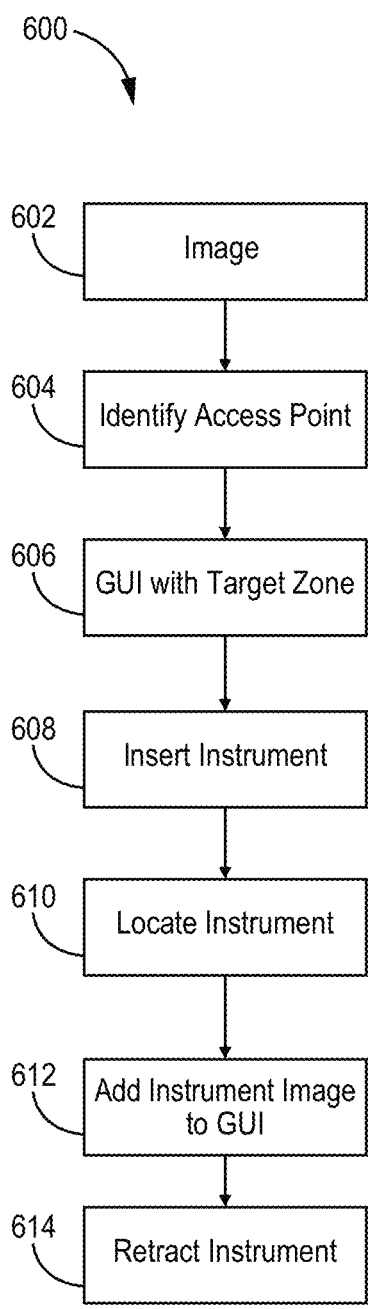
FIG. 7 is a flowchart of one embodiment of a method of implanting a mitral valve utilizing the system of FIG. 1.

In one or more embodiments, the system 10 can be utilized for implantation of a transcatheter mitral valve. For example, FIG. 7 is a flowchart of one embodiment of a method 600 of implanting a transcatheter mitral valve utilizing system 10. Although described in reference to system 10 of FIGS. 1-4, the method 600 can be utilized with any suitable system. In one or more embodiments, the controller 204 can be adapted to utilize the method 600. The heart of the patient can be imaged at 602 using any suitable technique, e.g., echocardiography. In one or more embodiments, the LV apex and the mitral valve can be imaged and provided in a bi-plane view to the clinician. An optimal access point near the apex can be identified at 604 that can provide a central, perpendicular trajectory of a catheter (e.g., instrument 130) through the mitral valve in both planes can be identified by the controller 204 and added to the GUI 300. For example, an access line or target path can be added to the GUI 300 and attached to one or more identified physiological landmarks such that the target path is registered with the landmark and moves along with the landmark in the GUI 300. An incision into the LV along the target path can be made, and an access sheath can be placed into the LV at 606.

The catheter can be inserted at 608 and located at 610 using any suitable technique or techniques. An augmented image of the catheter can be added to the GUI 300 at 612 based upon detection by the EM tracking system of one or more sensors disposed on the catheter. The catheter can be guided through the valve, and practice steering motions can be performed to aid the clinician to understand how hand motion correlates to tip motion.

Figure 9:
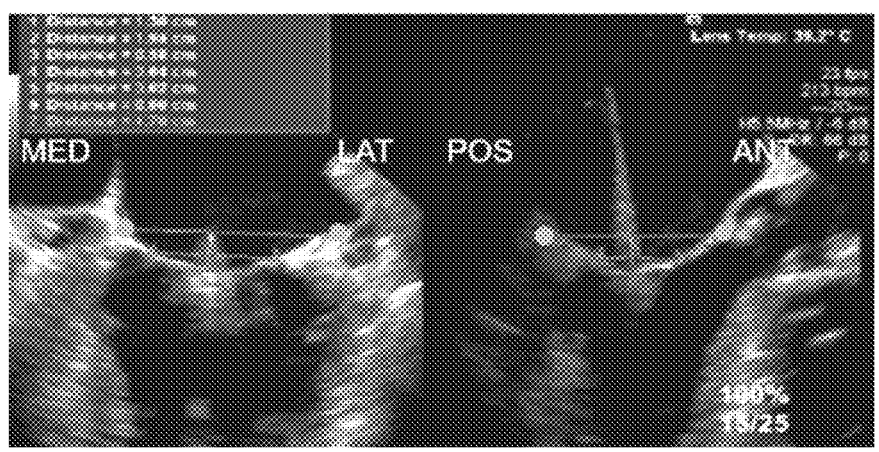
FIG. 9 is a schematic view of another embodiment of a graphical user interface.

The clinician or the system 10 can draw one or more target lines on the GUI 300 that overlay the real-time echocardiography image. For example, a line parallel to a mitral annulus line (e.g., 6 mm above the mitral annulus line) can be provided in the GUI 300 to provide a target landing line or zone. For example, FIG. 9 is a schematic view of a GUI 704 that includes the augmented mitral annulus line and the parallel target landing line or zone. This target landing line stays on the GUI 704 and dynamically moves with the surrounding anatomy once the echocardiography image goes live. Any suitable technique or techniques can be utilized to provide the target landing line, e.g., image recognition software or other soft tissue tracking techniques, machine learning, and/or AI. In one or more embodiments, the target landing line can change colors if the instrument 130 deviates from the desired trajectory or is disposed at the desired location.

In one or more embodiments, one or more target landing lines and/or one or more physiological landmark markers can remain visible in the GUI 704 even if the target region of the patient becomes obstructed or unavailable to the imaging system during the procedure. For example, image artifacts and shadowing of the anatomy due to reflection or obstruction of the ultrasound waves by the delivery catheter and/or the replacement valve can obstruct one or more portions of the target region of the patient to the ultrasound imaging system. In one or more embodiments, the controller can overlay or merge one or more reference images of the target region of the patient, which were acquired prior to the procedure, for example, with one or more live images from an imaging system of the target region of the patient during the procedure. In one or more embodiments, the controller 204 can overlay, e.g., in a semi-transparent fashion, or merge one or more reference images of the target region of the patient with one or more live images from the imaging system of the target region of the patient. In one or more embodiments, the controller is adapted to overlay or merge the reference image to the live image such that the reference image of the anatomy dynamically moves with the live image of the anatomy. In other words, the reference image is merged with the live image such that the reference image moves in registration with the live image in the GUI. The reference and live images can be merged using one or more common anatomical reference points within each image.

The reference image can remain visible in the GUI 704 even if one or more portions of the live image of the target region becomes obstructed or unavailable to the imaging system. In one or more embodiments, one or more target landing lines and/or one or more physiological landmark markers can remain visible in the GUI 704 registered to the reference image even one or more portions of the target region of the patient becomes obstructed or unavailable to the imaging system during the procedure.

The capsule of the catheter can be retracted at 614 to partially expose a replacement valve. The valve can be centered in the target area by the clinician while viewing the GUI 300. The catheter can be pulled back to place the valve in the target landing zone, and the valve can be deployed by completing retraction of the capsule. The catheter can be guided out of the patient's body through the middle of the replacement valve and into the sheath with the use of the GUI 704 at 614.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:
1. A system comprising:
    an ultrasound sensor configured to collect ultrasound image data representative of a region of a patient;
    an electromagnetic (EM) tracking system configured to collect EM tracking data representative of a position or orientation of each of the ultrasound sensor and an instrument relative to the region of the patient; and one or more processors configured to:
receive a reference ultrasound image of the region of the patient that was obtained when the instrument was located outside of the region;
receive the ultrasound image data from the ultrasound sensor;
receive the EM tracking data from the EM tracking system;
identify a physiological landmark of the region of the patient based on the ultrasound image data;
register the reference ultrasound image with the physiological landmark;
determine at least one of a position, orientation, or trajectory of the instrument based on the EM tracking data;
generate a graphical user interface showing at least one of the position, orientation, or trajectory of the instrument in relation to a real-time plane of the ultrasound image data, and a target zone that is registered with the physiological landmark and shown in real time, wherein the target zone is dynamically connected to the physiological landmark registered to the reference ultrasound image in the graphical user interface; and
overlay or merge the registered reference ultrasound image of the region of the patient to one or more real-time ultrasound images of the region of the patient as shown in the graphical user interface;
wherein the target zone moves with the physiological landmark as the registered reference ultrasound image moves with one more real-time ultrasound images of the region of the patient in the graphical user interface in real-time.

2. The system of claim 1, wherein the one or more processors is configured to overlay the registered reference ultrasound image with the plane of the ultrasound image data as shown in the graphical user interface.

3. The system of claim 1, wherein the reference ultrasound image comprises a semi-transparent reference ultrasound image.

4. The system of claim 1, wherein the one or more processors is further configured to:
determine the target zone based on user input data; and
generate the target zone in the graphical user interface based on the user input data.

5. The system of claim 1, wherein the one or more processors is further configured to:
determine whether at least one of the position, orientation, or trajectory of the instrument has changed; and
generate an updated graphical user interface showing at least one of an updated position, orientation, or trajectory of the instrument if it is determined that at least one of the position, orientation, or trajectory has changed.

6. The system of claim 1, wherein the one or more processors is further configured to:
determine an intersection between the instrument and the plane of the ultrasound image data; and
display an indicator of the intersection between the instrument and the plane of the ultrasound image data in the graphical user interface.

7. The system of claim 1, wherein the trajectory of the instrument shown in the graphical user interface has a length approximately equal to a length of the instrument.

8. The system of claim 1, wherein the instrument comprises one or more implantable devices, implant delivery devices, therapy delivery devices, surgical devices, mechanical circulatory support (e.g. LVAD) devices, coronary stent devices, heart valve devices, heart valve repair devices, cardiac ablation devices, cardiac lead devices, drug delivery devices, catheter delivery devices, and endoscopic delivery devices.

9. The system of claim 1, wherein the one or more processors is configured to generate the graphical user interface by displaying on a screen at least one of the position, orientation, or trajectory of the instrument in relation to a plane of the ultrasound image data, and a target zone that is registered with the physiological landmark.

10. The system of claim 1, wherein the graphical user interface comprises at least one marker representative of the physiological landmark.

11. A device comprising one or more processors configured to:
identify a physiological landmark of a region of a patient based on ultrasound image data;
register a reference ultrasound image with the physiological landmark;
determine at least one of a position, orientation, or trajectory of an instrument;
generate a graphical user interface showing at least one of the position, orientation, or trajectory of the instrument in relation to a real-time plane of the ultrasound image data, and a target zone that is registered with the physiological landmark and shown in real time, wherein the target zone is dynamically connected to the physiological landmark registered to the reference ultrasound image in the graphical user interface; and
overlay or merge the registered reference ultrasound image to one or more real-time ultrasound images of the region of the patient as shown in the graphical user interface;
wherein the target zone moves with the physiological landmark as the registered reference ultrasound image moves with one more real-time ultrasound images of the region of the patient in the graphical user interface in real-time.

12. The device of claim 11, wherein the one or more processors is configured to overlay the registered reference ultrasound image with the plane of the ultrasound image data as shown in the graphical user interface.

13. The device of claim 11, wherein the reference ultrasound image comprises a semi-transparent reference ultrasound image.

14. The device of claim 11, wherein the reference ultrasound image of the patient was obtained when the instrument was located outside of the region.

15. The device of claim 11, wherein the position, orientation, or trajectory of an instrument was determined based on the ultrasound image data, EM tracking data, or both.

16. The device of claim 11, wherein the one or more processors is further configured to:
determine the target zone based on user input data; and
generate the target zone in the graphical user interface data based on the user input data.

17. The device of claim 11, wherein the one or more processors is further configured to:
determine whether at least one of the position, orientation, or trajectory of the instrument has changed; and
generate an updated graphical user interface representing at least one of an updated position, orientation, or trajectory of the instrument if it is determined that at least one of the position, orientation, or trajectory has changed.

18. The device of claim 11, wherein the graphical user interface comprises at least one marker representative of the physiological landmark.

19. A method for tracking an instrument within a region of a patient, the method comprising:
- obtaining a reference ultrasound image representative of the region of the patient from an ultrasound sensor when the instrument is located outside of the region of the patient;
- obtaining ultrasound image data from the ultrasound sensor representing the region of the patient when at least a portion of the instrument is located within the region of the patient;
- obtaining electromagnetic (EM) tracking data from an EM tracking system representative of a position or orientation of each of the ultrasound sensor and the instrument relative to the region of the patient;
- identifying, with one or more processors, a physiological landmark of the region of the patient based on the ultrasound image data;
- determining, with the one or more processors, at least one of a position, orientation, or trajectory of the instrument based on the EM tracking data;
- registering, with the one or more processors, the reference ultrasound image with the physiological landmark;
- controlling, with the one or more processors, a display device to generate a graphical user interface showing at least one of the position, orientation, or trajectory of the instrument relative to a real-time plane of the ultrasound image data, and a target zone that is registered with the physiological landmark and shown in real time, wherein the target zone is dynamically connected to the physiological landmark registered to the reference ultrasound image in the graphical user interface; and
- controlling, with the one or more processors, the display device to overlay or merge the registered reference ultrasound image to one or more real-time ultrasound images of the region of the patient as shown in the graphical user interface;
- wherein the target zone moves with the physiological landmark as the registered reference ultrasound image moves with one more real-time ultrasound images of the region of the patient in the graphical user interface in real-time.

20. The method of claim 19, wherein the reference ultrasound image obtained comprises a semi-transparent reference ultrasound image.

21. The method of claim 19, wherein the region of the patient is a cardiac region.

22. The method of claim 19, wherein the graphical user interface comprises at least one marker representative of the physiological landmark.

\* \* \* \* \*